(12) United States Patent
Murray

(10) Patent No.: US 9,205,078 B2
(45) Date of Patent: Dec. 8, 2015

(54) N-METHYL-2-[3-((E)-2-PYRIDIN-2-YL-VINYL)-1H-INDAZOL-6-YLSULFANYL]-BENZAMIDE FOR THE TREATMENT OF CHRONIC MYELOGENOUS LEUKEMIA

(71) Applicant: PFIZER INC., New York, NY (US)

(72) Inventor: Brion William Murray, San Diego, CA (US)

(73) Assignee: PFIZER INC., New York, NY (US)

( * ) Notice: Subject to any disclaimer, the term of this patent is extended or adjusted under 35 U.S.C. 154(b) by 29 days.

(21) Appl. No.: 14/356,847

(22) PCT Filed: Nov. 5, 2012

(86) PCT No.: PCT/IB2012/056168
§ 371 (c)(1),
(2) Date: May 7, 2014

(87) PCT Pub. No.: WO2013/068909
PCT Pub. Date: May 16, 2013

(65) Prior Publication Data
US 2014/0288125 A1    Sep. 25, 2014

Related U.S. Application Data

(60) Provisional application No. 61/558,915, filed on Nov. 11, 2011.

(51) Int. Cl.
*A61K 31/4439*    (2006.01)

(52) U.S. Cl.
CPC .................................. *A61K 31/4439* (2013.01)

(58) Field of Classification Search
CPC .................................................. A61K 31/4439
USPC .......................................................... 514/338
See application file for complete search history.

(56) References Cited

U.S. PATENT DOCUMENTS

| | | | |
|---|---|---|---|
| 6,177,401 B1 | 1/2001 | Ullrich |
| 6,534,524 B1 | 3/2003 | Kania |
| 6,884,890 B2 | 4/2005 | Kania |
| 7,141,581 B2 | 11/2006 | Bender |
| 7,232,910 B2 | 6/2007 | Ewanicki |
| 8,791,140 B2 | 7/2014 | Campeta |
| 2004/0224988 A1 | 11/2004 | Freddo |
| 2006/0091067 A1 | 5/2006 | Fan |
| 2006/0094763 A1 | 5/2006 | Ye |
| 2007/0203196 A1 | 8/2007 | Ewanicki |
| 2008/0274192 A1 | 11/2008 | Friesen |
| 2014/0248347 A1 | 9/2014 | Gierer |

FOREIGN PATENT DOCUMENTS

| | | |
|---|---|---|
| WO | 2006048745 A1 | 11/2006 |
| WO | 2011038467 A1 | 4/2011 |

OTHER PUBLICATIONS

Davis, M., et al., "Comprehensive analysis of kinase inhibitor selectivity," 2011, Nature Biotechnology, 1046-1052, vol. 29, No. 11.
International Preliminary Report on Patentability for International Appln. No. PCT/IB2012/056168 issued May 13, 2014.
International Search Report for International Appln. No. PCT/IB2012/056168 completed on Feb. 25, 2013; Mailing Date of Mar. 25, 2013.
Jamieson, C., "Chronic Myeloid Leukemia Stem Cells," 2008, Hematology, 436-442, vol. 1.
O'Hare, T., et al., "Targeting the BCR-ABL Signaling Pathway in Therapy-Resistant Philadelphia Chromosome-Positive Leukemia," 2011, Clinical Cancer Research, 212-221, vol. 17., No. 2.
Weisberg, E., et al., "Second generation inhibitors of BCR-ABL for the treatment of imatinib-resistant chronic myeloid leukaemia," 2007, Nature Reviews Cancer, 345-356, vol. 7, No. 5.

*Primary Examiner* — Raymond Henley, III
(74) *Attorney, Agent, or Firm* — Suzanne M. Bates; Stephen D. Prodnuk

(57) ABSTRACT

The present invention relates to a method of treating chronic myelogenous leukemia in a subject comprising administering to the subject a compound, such as N-methyl-2-[3-((E)-2-pyridin-2-yl-vinyl)-1H-indazol-6-ylsulfanyl]-benzamide, that inhibits the T315I mutation in BCR-ABL tyrosine kinase, or a pharmaceutically acceptable salt thereof. The present invention also relates to a pharmaceutical composition comprising a compound such as N-methyl-2-[3-((E)-2-pyridin-2-yl-vinyl)-1H-indazol-6-ylsulfanyl]-benzamide, that inhibits the T315I mutation in BCR-ABL tyrosine kinase, or a pharmaceutically acceptable salt thereof, and a pharmaceutically acceptable carrier or diluent.

7 Claims, No Drawings

N-METHYL-2-[3-((E)-2-PYRIDIN-2-YL-VINYL)-1H-INDAZOL-6-YLSULFANYL]-BENZAMIDE FOR THE TREATMENT OF CHRONIC MYELOGENOUS LEUKEMIA

CROSS-REFERENCE TO RELATED APPLICATIONS

This application is a §371 filing of PCT/IB2012/056168 filed Nov. 5, 2012, which claims the benefit of priority to United States Provisional Application No. 61/558,915, filed Nov. 11, 2011; the entire contents of which are incorporated herein by reference.

FIELD OF THE INVENTION

The present invention relates to a method of treating chronic myelogenous leukemia in a subject comprising administering to the subject a compound, such as N-methyl-2-[3-((E)-2-pyridin-2-yl-vinyl)-1H-indazol-6-ylsulfanyl]-benzamide, that inhibits the T315I mutation in BCR-ABL tyrosine kinase, or a pharmaceutically acceptable salt thereof. The present invention also relates to a pharmaceutical composition comprising a compound such as N-methyl-2-[3-((E)-2-pyridin-2-yl-vinyl)-1H-indazol-6-ylsulfanyl]-benzamide, that inhibits the T315I mutation in BCR-ABL tyrosine kinase, or a pharmaceutically acceptable salt thereof, and a pharmaceutically acceptable carrier or diluent.

BACKGROUND OF THE INVENTION

Chronic myelogenous leukemia (CML) is a hematological stem cell disorder caused by increased and unregulated growth of myeloid cells in the bone marrow, and the accumulation of excessive white blood cells. Abelson tyrosine kinase (ABL) is a non-receptor tyrosine kinase involved in cell growth and proliferation and is usually under tight control. However, 95% of CML patients have the ABL gene from chromosome 9 fused with the breakpoint cluster (BCR) gene from chromosome 22, resulting in a short chromosome known as the Philadelphia chromosome. This Philadelphia chromosome is responsible for the production of the BCR-ABL fusion protein, a constitutively active tyrosine kinase that causes uncontrolled cellular proliferation. An ABL inhibitor, imatinib, was approved by the FDA for the treatment of CML, and is currently used as first-line therapy. It has been reported that 80% of CML patients respond to imatinib with under 3% progressing to advanced disease within 5 years (Schwartz, P. A., et al., Bioorg Chem 39: 192 (2011)). The durability of clinical response, however, is adversely affected by the development of resistance to drug therapy. In 2001, the first imatinib resistant mutant was reported as a T315I BCR-ABL "gatekeeper" mutation. Subsequent analysis revealed that reoccurrence arises with over fifty-five documented point mutations occurring throughout the catalytic and regulatory domains, with a large percentage located in the G-loop and the gatekeeper position (Id.). Clinical success has been achieved towards most mutations, but there is no approved agent directed towards the gatekeeper T315I mutation (O'Hare, T., et al., Clin Cancer Res 17: 212 (2011)).

The compound, N-methyl-2-[3-((E)-2-pyridin-2-yl-vinyl)-1H-indazol-6-ylsulfanyl]-benzamide or 6-[2-(methylcarbamoyl)phenylsulfanyl]-3-E-[2-(pyridin-2-yl)ethenyl]indazole, of the following structure:

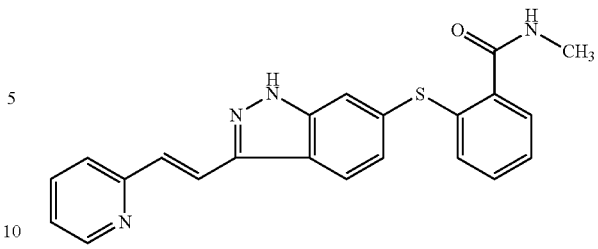

is known as axitinib or AG-013736.

Axitinib is a potent and selective inhibitor of vascular endothelial growth factor (VEGF) receptors 1, 2 and 3. These receptors are implicated in pathologic angiogenesis, tumor growth, and metastatic progression of cancer. Axitinib has been shown to potently inhibit VEGF-mediated endothelial cell proliferation and survival (Hu-Lowe, D. D., et al., Clin Cancer Res 14: 7272-7283 (2008); Solowiej, S., et al., Biochemistry 48: 7019-31 (2009)). Clinical trials are currently on-going to study the use of axitinib for the treatment of various cancers, including liver cancer, melanoma, mesothelioma, non-small cell lung cancer, prostate cancer, renal cell carcinoma, soft tissue sarcomas and solid tumors. Inlyta® (axitinib) has been approved in the United States, Europe, Japan and other jurisdictions for the treatment of renal cell carcinoma.

Axitinib, as well as pharmaceutically acceptable salts thereof, is described in U.S. Pat. No. 6,534,524. Methods of making axitinib are described in U.S. Pat. Nos. 6,884,890 and 7,232,910, in U.S. Publication Nos. 2006-0091067 and 2007-0203196 and in International Publication No. WO 2006/048745. Dosage forms of axitinib are described in U.S. Publication No. 2004-0224988. Polymorphic forms and pharmaceutical compositions of axitinib are also described in U.S. Publication Nos. 2006-0094763, 2008-0274192 and 2010-0179329. The patents and patent applications listed above are incorporated herein by reference.

SUMMARY OF THE INVENTION

Each of the embodiments described below can be combined with any other embodiment described herein not inconsistent with the embodiment with which it is combined.

Some embodiments relate to a method of treating chronic myelogenous leukemia in a subject comprising administering to the subject a compound that inhibits the T315I mutation in BCR-ABL tyrosine kinase, or a pharmaceutically acceptable salt thereof.

Additional embodiments relate to the method described above, wherein the subject has the T315I mutation in BCR-ABL tyrosine kinase.

Further embodiments relate to the methods described above, wherein the compound is N-methyl-2-[3-((E)-2-pyridin-2-yl-vinyl)-1H-indazol-6-ylsulfanyl]-benzamide, or a pharmaceutically acceptable salt thereof.

More embodiments relate to a method of treating chronic myelogenous leukemia in a subject comprising administering to the subject a compound that inhibits the T315I mutation in BCR-ABL tyrosine kinase, wherein the compound is N-methyl-2-[3-((E)-2-pyridin-2-yl-vinyl)-1H-indazol-6-ylsulfa-nyl]-benzamide, or a pharmaceutically acceptable salt thereof.

Additional embodiments relate to a method of treating chronic myelogenous leukemia in a subject having the T315I mutation in BCR-ABL tyrosine kinase, comprising administering to the subject a compound that inhibits the T315I mutation in BCR-ABL tyrosine kinase, or a pharmaceutically acceptable salt thereof.

Further embodiments relate to a method of treating chronic myelogenous leukemia in a subject having the T315I mutation in BCR-ABL tyrosine kinase, comprising administering to the subject a compound, which is N-methyl-2-[3-((E)-2-pyridin-2-yl-vinyl)-1H-indazol-6-ylsulfanyl]-benzamide, or a pharmaceutically acceptable salt thereof.

Additional embodiments relate to a method of treating chronic myelogenous leukemia in a subject having the T315I mutation in BCR-ABL tyrosine kinase, comprising administering to the subject a compound that inhibits the T315I mutation in BCR-ABL tyrosine kinase, wherein the compound is N-methyl-2-[3-((E)-2-pyridin-2-yl-vinyl)-1H-indazol-6-ylsulfanyl]-benzamide,or a pharmaceutically acceptable salt thereof.

Some embodiments relate to a pharmaceutical composition comprising a compound that inhibits the T315I mutation in BCR-ABL tyrosine kinase, or a pharmaceutically acceptable salt thereof, and a pharmaceutically acceptable carrier or diluent.

Further embodiments relate to the pharmaceutical composition described above, wherein the compound is N-methyl-2-[3-((E)-2-pyridin-2-yl-vinyl)-1H-indazol-6-ylsulfanyl]-benzamide, or a pharmaceutically acceptable salt thereof.

Additional embodiments relate to a pharmaceutical composition comprising a compound that inhibits the T315I mutation in BCR-ABL tyrosine kinase, wherein the compound is N-methyl-2-[3-((E)-2-pyridin-2-yl-vinyl)-1H-indazol-6-ylsulfanyl]-benzamide, or a pharmaceutically acceptable salt thereof, and a pharmaceutically acceptable carrier or diluent.

Further embodiments relate to a pharmaceutical composition for treating chronic myelogenous leukemia in a subject comprising a compound that inhibits the T315I mutation in BCR-ABL tyrosine kinase, wherein the compound is N-methyl-2-[3-((E)-2-pyridin-2-yl-vinyl)-1H-indazol-6-ylsulfanyl]-benzamide, or a pharmaceutically acceptable salt thereof, and a pharmaceutically acceptable carrier or diluent.

Additional embodiments relate to a pharmaceutical composition for treating chronic myelogenous leukemia in a subject having the T315I mutation in BCR-ABL tyrosine kinase, comprising a compound that inhibits the T315I mutation in BCR-ABL tyrosine kinase, wherein the compound is N-methyl-2-[3-((E)-2-pyridin-2-yl-vinyl)-1H-indazol-6-ylsulfanyl]-benzamide, or a pharmaceutically acceptable salt thereof, and a pharmaceutically acceptable carrier or diluent.

DETAILED DESCRIPTION OF THE INVENTION

The following abbreviations may be used herein: ABLtide (synthetic peptide sequence ([5-carboxyfluorescein]-EAIYAAPFAKKK-COHN$_2$) based on the C-terminus of ABL); ADP (adenosine diphosphate); ATP (adenosine triphosphate); BRIJ-35 (polyoxyethylene lauryl ether); BSA (bovine serum albumin); DMSO (dimethylsulphoxide); dithiothreitol (DTT); EGTA (ethylene glycol tetraacetic acid); ELISA (enzyme linked immunosorbent assay); FBS (fetal bovine serum); HEPES (4-(2-hydroxyethyl)piperazine-1-ethanesulfonic acid or N-(2-hydroxyethyl)piperazine-N-(2-ethanesulfonic acid)); NADH (reduced form of nicotinamide adenine dinucleotide or nicotinamide adenine dinucleotide plus hydrogen); RPMI (Roswell Park Memorial Institute); SDS (sodium dodecylsulfate); Tyr (tyrosine); Tyr 02 peptide (peptide sequence (EAIYAAPF)); and WT (wild-type).

The phrase "pharmaceutically acceptable salt(s)", as used herein, unless otherwise indicated, includes salts of acidic or basic groups which may be present in the compounds of described herein. The compounds described herein that are basic in nature are capable of forming a wide variety of salts with various inorganic and organic acids. The acids that may be used to prepare pharmaceutically acceptable acid addition salts of such basic compounds described herein are those that form non-toxic acid addition salts, e.g., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts. The compounds described herein that include a basic moiety, such as an amino group, may form pharmaceutically acceptable salts with various amino acids, in addition to the acids mentioned above.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above.

The term "subject", as used herein, may be a human or non-human mammal (e.g., rabbit, rat, mouse, horse, monkey, other lower-order primate, etc.). In an embodiment, the term "subject" refers to a human.

Administration of the compounds described herein can be effected by any method or route that enables delivery of the compounds to the site of action. These methods include oral routes, intraduodenal routes, parenteral injection (including intravenous, subcutaneous, intramuscular, intravascular or infusion), topical, and rectal administration.

The dosage administered will, of course, vary with the compound employed, the mode of administration, the treatment desired and the disorder indicated. The dosage may be as a single dose or according to a multiple dose regimen, alone or in combination with other compounds, agents or substances. One of ordinary skill in the art would be able to determine such amounts based on such factors as a subject's size, the severity of a subject's symptoms, and the particular composition or route of administration selected. The daily dosage of the compound, or pharmaceutically acceptable salt thereof, may be in the range from 0.1 mg to 1 gram, preferably 0.1 mg to 250 mg, more preferably 0.1 mg to 50 mg.

In some embodiments, satisfactory results are obtained when axitinib, or a pharmaceutically acceptable salt thereof, is administered at a daily dosage of from of from about 0.01 mg/kg to about 0.4 mg/kg of body weight, optionally given in divided doses two to four times a day. The total daily dosage is projected to be from about 0.1 to about 25 mg, preferably from about 1 mg to about 10 mg two times a day, and more preferably from about 2 to about 10 mg two times a day. This dosage regimen may be adjusted to provide the optimal therapeutic response. For example, several divided doses may be administered daily or the dose may be proportionally reduced or increased as indicated by the exigencies of the therapeutic situation.

The pharmaceutical composition may, for example, be in a form suitable for oral administration as a tablet, capsule, pill, powder, sustained release formulation, solution, or suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition includes a conventional pharmaceutically acceptable carrier or excipient and a compound described herein as an active ingredient. In addition, it may include other medicinal or pharmaceutical agents, carriers, or adjuvants.

Exemplary parenteral administration forms include solutions or suspensions of active compounds in sterile aqueous solutions, for example, aqueous propylene glycol or dextrose solutions. Such dosage forms can be suitably buffered, if desired.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials, therefore, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

EXAMPLES

Example 1

ABL1 Kinase Spectrophotometric Coupled Enzymatic Assay

Axitinib was tested in a spectrophotometric coupled enzymatic assay used to measure ABL1 and ABL1 [T315I] enzymatic activity, which has been previously described (Solowiej, J., et al., *Biochemistry*, 48: 7019-7031 (2009)). The kinase-catalyzed production of ADP that accompanies phosphoryl transfer of the γ-phosphate of ATP to the tyrosine residue in human minigastrin 1 peptide (LEEEEAYGW-MDF-NH2) was coupled to the oxidation of NADH through the activities of pyruvate kinase (PK) and lactate dehydrogenase (LDH). Concomitant with the production of ADP is the β-NADH (reduced form of nicotinamide adenine dinucleotide) conversion to β-NAD$^+$ (oxidized form of nicotinamide adenine dinucleotide) which was monitored by the decrease in absorbance at 340 nm ($\epsilon$=6220 cm$^{-1}$M$^{-1}$) using a Beckman DU800 spectrophotometer at 25° C. Typical reaction solutions contained 2 mM phosphoenolpyruvate, 0.28 mM NADH, 50 mM MgCl$_2$, 2 mM DTT, ATP, minigastrin, 15 units/mL PK, 15 units/mL LDH in 25 mM HEPES, pH 7.5. To determine kinetic parameters, ATP was varied from 5 to 1000 µM. Assays were initiated with the addition of 20 nM full length ABL1 or 100 nM ABL1 [T315I]. The same coupled enzymatic assay format was used for percent inhibition and K$_i$ determinations. Axitinib was prepared in 100% DMSO. The final concentration of DMSO in the assay was 1%. The concentration of ATP was 3× k$_m$ (165 µM ABL1 and 40 µM ABL1 [T315I]. The concentration of minigastrin was 500 µM. K$_i$ determinations were made from a plot of the fractional velocity as a function of inhibitor concentration fit to the quadratic equation for competitive inhibition "Morrison equation" with the enzyme concentration as a variable (Morrison, J. F., *Biochimica et biophysica acta*, 185: 269-286 (1969)).

As shown in Table 1, the % inhibition data generated for axitinib indicated a shift in potency toward the ABL1 [T315I] mutation.

TABLE 1

Axitinib Inhibitory Potencies Toward Enzymatic Activities of ABL1 Proteins Determined by the ABL1 Kinase Spectrophotometric Coupled Enzymatic Assay

| Kinase | % Inh @ 20 nM |
|---|---|
| ABL WT | 25 |
| ABL(T315I) | 80 |

Example 2

ABL1 Kinase Mobility-Shift Assay

Axitinib was tested with the Caliper LabChip3000 assay (Caliper Life Science, Hopkinton, Mass.), which is a mobility-shift assay (MSA) that combines the basic principles of capillary electrophoresis in a micro-fluidic environment. Axitinib was prepared in 100% DMSO, diluted to 25% DMSO with 20 mM HEPES pH 7.5, and added to the reaction for a final DMSO concentration of 6%. Inhibitor concentrations varied from 1.0 µM to 0.00003 µM. Typical reactions were 20 µL, contained ABL1 or ABL1 [T315I], ATP (ABL1; 25 µM and ABL1 [T315I]; 5 µM), 1.0 µM ABLtide, 5 mM MgCl$_2$, 2 mM DTT, 0.01% Triton® X-100 (Sigma-Aldrich, St. Louis, Mo.), 6% DMSO in 20 mM HEPES pH 7.5. The mixture was incubated in a 384-well polypropylene plate at room temperature for an hour and terminated by the addition of 60 µL of QuickScout Screening Assist MSA Buffer (Carna Biosciences, Kobe, Japan). The reaction mixture was applied to a LabChip3000 system, and the product /substrate peptide peaks were separated. The kinase reaction was quantitated by the product ratio calculated from peak heights of product (P) and substrate (S) peptides (P/(P+S)).

As shown in Table 2, the data generated for axitinib demonstrated a 14 fold shift in potency for the gatekeeper mutation versus the wild type enzyme.

TABLE 2

Axitinib Inhibitory Potencies Toward Enzymatic Activities of ABL1 Proteins Determined by the ABL1 Kinase Mobility-Shift Assay

| Kinase | IC$_{50}$(nM) |
|---|---|
| ABL WT | 7.784 |
| ABL(T315I) | 0.5511 |

Example 3

ABL1 Kinase Z'-LYTE® Screening Assay

Axitinib was tested using a Z'-LYTE Screening Protocol (Invitrogen, Carlsbad, Calif.). Axitinib was prepared in 100% DMSO, and added to the reaction for a final DMSO concentration of 1%. Inhibitor concentrations varied from 1.0 µM to 0.00003 µM. Typical reactions were 10 µL, contained ABL1 or ABL1 [T315I], ATP (ABL1; 10 µM and ABL1 [T315I]; 5 µM), 2.0 µM Tyr 02 peptide, 10 mM $MgCl_2$, 1.0 mM EGTA, 0.01% BRIJ-35, 1% DMSO in 50 mM HEPES pH 7.5. The mixture was incubated in a 384-well polypropylene plate at room temperature for an hour and terminated by the addition of 5 µL of a 1:64 dilution of the development reagent utilized with Z'-LYTE® Screening Protocol, followed by a 30 second shake. The development reaction was allowed to incubate at room temperature for one hour. The resulting fluorescence was read on a fluorescence plate reader and the data were analyzed.

As shown in Table 3, the data generated for axitinib demonstrated a 6.2 fold shift in potency for the gatekeeper mutation vs. the wild type enzyme.

TABLE 3

Axitinib Inhibitory Potencies Toward Enzymatic Activities of ABL1 Proteins Determined by the ABL1 Kinase Z'-LYTE ® Screening Assay

| Kinase | $IC_{50}$(nM) |
|---|---|
| ABL WT | 2.6 |
| ABL(T315I) | 0.418 |

Example 4

BCR-ABL Engineered BaF3 Cell Autophosphorylation ELISA

BaF3 WT BCR-ABL and BaF3-T315I mutant BCR-ABL cell lines were obtained from Oregon Health and Science University and grown in RPMI-1640 medium supplemented with 10% FBS and 1% penicillin streptomycin (100× stock=5000 units of penicillin and 5000 µg of streptomycin per mL). For the c-ABL phospho-Tyr ELISA, cells were pipeted into a 50 mL tube, centrifuged at 1000 RPM, and the cell pellet was re-suspended in assay medium (RPMI-1640 with 0.1% FBS, 0.05% BSA wt/vol, and 1% penicillin streptomycin). The cells were counted using an Innovatis Cedex Cell Counter, seeded into a 96 well flat bottom plate in assay medium at 40,000 cells per well and incubated 2 hours with assay medium at 37° C., 5% $CO_2$, 95% air. Axitinib was dissolved in 100% DMSO to make 10 mM stocks. Axitinib was then diluted in 100% DMSO in a polypropylene 96 well plate using 3 fold serial dilution. Control wells contained 100% DMSO without test compound (uninhibited controls). The DMSO drug dilution plate was diluted 40 fold into assay medium (RPMI-1640 with 0.1% FBS, 0.05% BSA wt/vol, and 1% penicillin streptomycin) to yield a 5× drug source plate for the assay. Twenty five microliters was transferred from the 5× source plate to the cell assay plate and the assay plate was incubated with axitinib for an additional 2 hours at 37° C., 5% $CO_2$, 95% air. Following this incubation, the cells were centrifuged at 1500 RPM for 5 mins and 80 µL of the supernatant removed. Cells were lysed by adding 100 µL per well of freshly prepared Cell Signaling Technology lysis buffer (#9803) supplemented with 1% SDS, protease inhibitors (Sigma P8340), and phosphatase inhibitors (Sigma P0044 and Sigma P5726). The cell assay plate with lysis buffer was shaken for 10 min at 4° C. and then 100 µL of cell lysate from each well was transferred to a goat anti-rabbit 96 well ELISA plate (Pierce #15135) which was previously incubated with rabbit anti-c-ABL antibody (Cell Signaling Technology #2862) diluted 1:200 in blocking buffer (Pierce StartingBlock). The cell lysate was incubated with the anti-c-ABL coated ELISA plate for 1 hour at room temperature and then washed 4 times with Cell Signaling Technology ELISA Wash Buffer (from kit #7903). The final wash was removed by inverting the plate and 100 µL of mouse monoclonal (IgG2b)anti-phospho-Tyr antibody (Santa Cruz Biotechnology SC508 HRP) diluted 1:5000 was added to each well. The ELISA plate was then incubated for 45 min at room temperature with 100 µL per well. The plate was washed 4 times as described above, the final wash removed, and 100 µL of TMB substrate (Santa Cruz Biotechnology SC286967) was added to each well. The plate was read at 655 nm during color development or stopped by adding 50-100 µL per well of 0.16 M sulfuric acid stop solution and read at 450 nm.

As shown in Table 4, the data generated for axitinib demonstrated an 8.6 fold shift in potency for the gatekeeper mutation vs. the wild type enzyme.

TABLE 4

Axitinib Inhibitory Potencies Toward the Inhibition of T315I Mutation of BCR-ABL Autophosphorylation Determined by the BCR-ABL Engineered BaF3 Cell ELISA

| Kinase | $IC_{50}$(nM) |
|---|---|
| ABL WT | 177 ± 58 (n = 2) |
| ABL(T315I) | 20.7 ± 4.6 (n = 3) |

Example 5

BCR-ABL Engineered BaF3 Cell Proliferation Assay (Method A)

BaF3 WT BCR-ABL and BaF3-T315I mutant BCR-ABL cell lines were obtained from Oregon Health and Science University and grown in RPMI-1640 with 10% FBS as described above. For the proliferation assay, cells were pipeted into a 50 mL tube, centrifuged at 1000 RPM, and the cell pellet was re-suspended in RPMI-1640 with 1% FBS, and 1% penicillin streptomycin. The cells were counted using an Innovatis Cedex Cell Counter and seeded into a 96 well flat bottom plate at 1,500 cells per well. Axitinib was serially diluted in 100% DMSO as described above and then diluted 40 fold into RPMI-1640 with 1% FBS and 1% penicillin streptomycin to yield a 5× source plate. Twenty five microliters was transferred from the 5× source plate to the cell assay plate and the cells incubated with axitinib for 4 days at 37° C., 5% $CO_2$, 95% air. On Day 4 post drug addition, the cell assay plate was centrifuged at 1000 RPM for 2 mins, 80 µL of supernatant was removed from each well, and 100 µL of fresh medium was added to each well. Fifteen µL of 1 mg/mL Resazurin (Sigma R7017) was then added to each well and the cell assay plate was incubated for 6 hour at 37° C., 5% $CO_2$, 95% air. The fluorescent signal was read using 530 nm excitation and 595 nm emission wavelengths.

As shown in Table 5, the data generated for axitinib demonstrated a 10 fold shift in potency for the gatekeeper mutation vs. the wild type enzyme.

TABLE 5

Axitinib Inhibitory Potencies Toward the T315I Mutation of BCR-ABL Mediated Cell Proliferation Determined by the BCR-ABL Engineered BaF3 Cell Proliferation Assay

| Kinase | $IC_{50}$(nM) |
|---|---|
| ABL WT | 217 ± 46 (n = 2) |
| ABL(T315I) | 21.0 ± 3.6 (n = 3) |

Example 6

Wild-type BCR-ABL CML Cell Proliferation Assay

Using the method of Example 5, Table 6 shows the data generated for axitinib in wild-type BCR-ABL CML cell lines.

TABLE 6

Axitinib Inhibitory Potencies Toward Wild-type BCR-ABL Mediated Cell Proliferation Determined by the BCR-ABL CML Cell Proliferation Assay

| WT BCR-ABL CML cell line | $IC_{50}$(nM) |
|---|---|
| MEG01 (1% FBS) | 105 |
| MEG01 (10% FBS) | 314 |
| K562 (10% FBS) | 323 |

Example 7

BCR-ABL Engineered BaF3 Cell Proliferation Assay (Method B)

Using the previously published method (le Coutre P, Mologni L, Cleris L, Marchesi E, Buchdunger E, Giardini R, Formelli F, Gambacorti-Passerini C., "In vivo eradication of human BCR/ABL-positive leukemia cells with an ABL kinase inhibitor." J Natl Cancer Inst. 1999 Jan 20;91(2):163-8.), cells were seeded at a concentration of $10^4$ cells/well (10% FBS) in 96-well round bottom cell culture plates with complete medium and in presence of increasing concentration of inhibitors (range 10 to 0 μM). Cell proliferation was measured at 72 hours using the tritiated thymidine incorporation assay as described previously. The only difference from the previously disclosed method was that the labeling time was 8 hours (64 hours after seeding, the cells were labelled with $^3$H thyimidine, incubate for 8 hours and harvest). Each test was performed in quadruplicate and repeated at least twice. Calculation of $IC_{50}$ values was performed using Graphpad Prism software.

As shown in Table 7, the data generated for axitinib demonstrated a 8.4 fold shift in potency for the gatekeeper mutation vs. the wild type enzyme.

TABLE 7

Axitinib Inhibitory Potencies Toward the T315I Mutation of BCR-ABL Determined by the BCR-ABL Engineered BaF3 Cell Proliferation Assay

| Kinase | $IC_{50}$(nM) |
|---|---|
| ABL WT | 823 |
| ABL(T315I) | 98 |

I claim:

1. A method of treating chronic myelogenous leukemia in a subject comprising administering to the subject a compound that inhibits the T315I mutation in BCR-ABL tyrosine kinase, wherein the compound is N-methyl-2-[3-((E)-2-pyridin-2-yl-vinyl)-1H-indazol-6-ylsulfanyl]-benzamide, or a pharmaceutically acceptable salt thereof.

2. The method of claim 1, wherein the subject is human.

3. A method of treating chronic myelogenous leukemia in a subject having the T315I mutation in BCR-ABL tyrosine kinase, comprising administering to the subject a compound, which is N-methyl-2-[3-((E)-2-pyridin-2-yl-vinyl)-1H-indazol-6-ylsulfanyl]-benzamide, or a pharmaceutically acceptable salt thereof.

4. The method of claim 3, wherein the subject is human.

5. A method of treating chronic myelogenous leukemia in a subject having the T315I mutation in BCR-ABL tyrosine kinase, comprising administering to the subject a compound that inhibits the T315I mutation in BCR-ABL tyrosine kinase, wherein the compound is N-methyl-2-[3-((E)-2-pyridin-2-yl-vinyl)-1H-indazol-6-ylsulfanyl]-benzamide, or a pharmaceutically acceptable salt thereof.

6. The method of claim 5, wherein the subject is human.

7. A pharmaceutical composition for treating chronic myelogenous leukemia in a subject comprising a compound that inhibits the T315I mutation in BCR-ABL tyrosine kinase, wherein the compound is N-methyl-2-[3-((E)-2-pyridin-2-yl-vinyl)-1H-indazol-6-ylsulfanyl]-benzamide, or a pharmaceutically acceptable salt thereof, and a pharmaceutically acceptable carrier or diluent.

* * * * *